United States Patent [19]

Turbe

[11] Patent Number: 4,689,995

[45] Date of Patent: Sep. 1, 1987

[54] METHOD AND APPARATUS FOR THE NON-DESTRUCTIVE TESTING OF RAILROAD TRACK RAILS

[75] Inventor: Jean Pierre Turbe, Nanteuil-les-Meaux, France

[73] Assignee: Societe Nationale des Chemins de Fer Francais, Paris, France

[21] Appl. No.: 807,881

[22] PCT Filed: Mar. 22, 1985

[86] PCT No.: PCT/FR85/00058
§ 371 Date: Nov. 19, 1985
§ 102(e) Date: Nov. 19, 1985

[87] PCT Pub. No.: WO85/04484
PCT Pub. Date: Oct. 10, 1985

[30] Foreign Application Priority Data

Mar. 23, 1984 [FR] France .................. 84 04523

[51] Int. Cl.⁴ .................. G01N 29/04
[52] U.S. Cl. .................. 73/636; 73/634
[58] Field of Search .................. 73/634, 635, 636

[56] References Cited

U.S. PATENT DOCUMENTS

| | | | |
|---|---|---|---|
| 3,028,751 | 4/1962 | Joy | 73/636 |
| 4,044,594 | 8/1977 | Owens et al. | 73/636 |
| 4,165,648 | 8/1979 | Pagano | 73/636 |
| 4,174,636 | 11/1979 | Pagano | 73/636 |
| 4,235,112 | 11/1980 | Kaiser | 73/636 |

FOREIGN PATENT DOCUMENTS 1545324 5/1979 United Kingdom .

Primary Examiner—Howard A. Birmiel
Attorney, Agent, or Firm—Sughrue, Mion, Zinn, Macpeak and Seas

[57] ABSTRACT

A device for inspecting a rail 2 of a railway track comprises a truck 1 running on the rail and carried by a railway vehicle. The truck carries at least one ultrasonic emitter and/or receiver probe 7, 8 in contact with the upper surface of the rail. At least one probe 8 is displaceable on a slide 6 while another probe 7 is fixed to the truck 1. The device comprises a jack 9 for displacing the probe 8 as a function of variations of the energy received by the receiver probe to compensate for fluctuations in the height of the rail.

8 Claims, 3 Drawing Figures

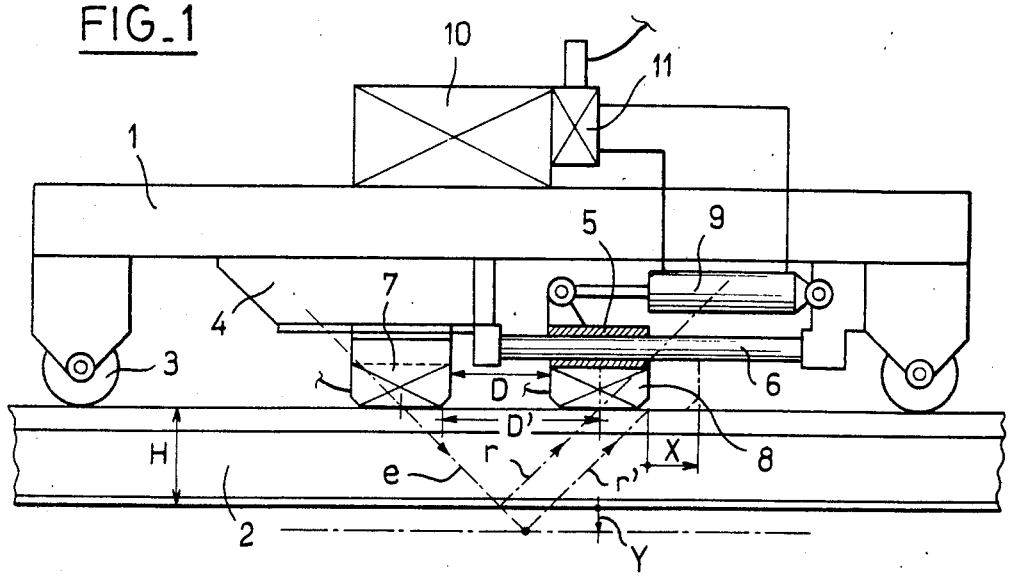
FIG_1
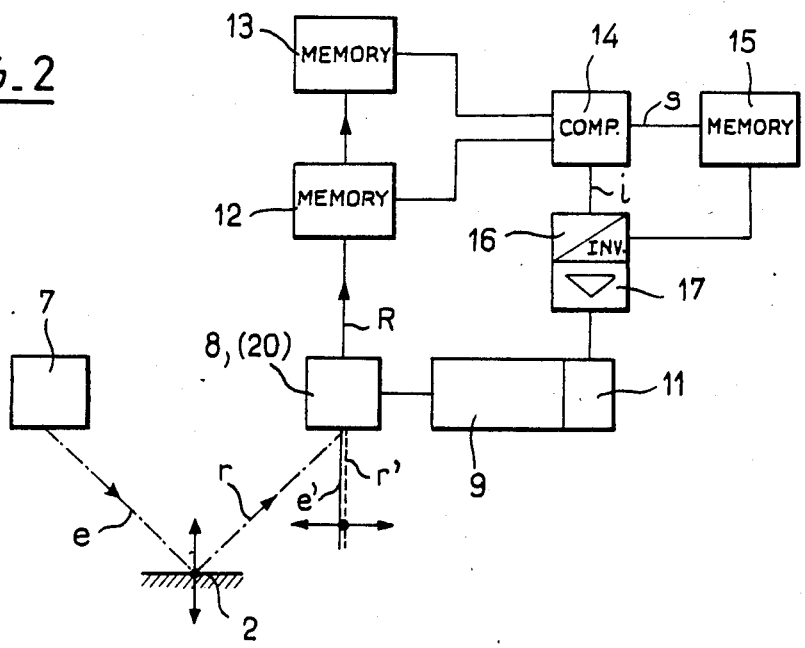
FIG_2

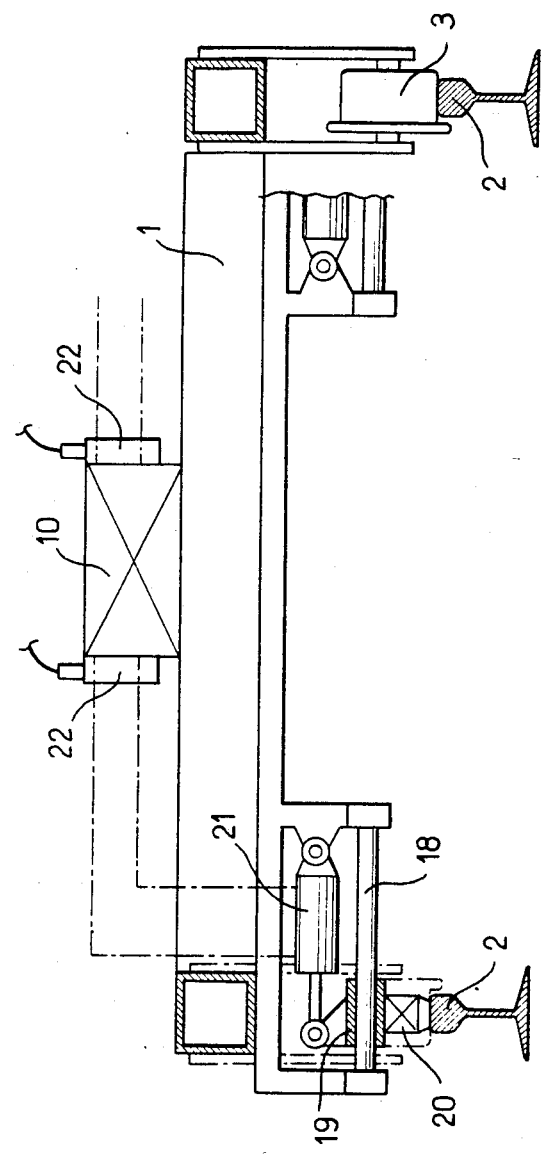
FIG_3

METHOD AND APPARATUS FOR THE NON-DESTRUCTIVE TESTING OF RAILROAD TRACK RAILS

BACKGROUND OF THE INVENTION

This invention relates to the testing of rails of railroad tracks, and more particularly to a method and apparatus for the non-destructive testing of the rails of railroad tracks in situ and continuously. device for the implementation of such a process.

The dynamic overloads and stresses to which the track is subjected cause the development of internal faults in the rail, such as oval flaws, horizontal, transverse or longitudinal cracks, star-shaped cracks, etc.

It is important to be able to detect these faults on the track using a non-destructive method, in order to be able to change defective sections of rail in time.

The most widely used method of non-destructive testing of the internal state of rail on the track is the sounding of the rail by ultrasonics. This technique consists in placing in contact with the rail head transmitting, receiving or transmitting-receiving probes, the orientation of which is adapted to the types of fault being looked for.

The picked up echoes of the transmitted ultrasonics are usually displayed on cathode ray screens. These echoes are also recorded graphically, which enables the position and type of the faults detected to be determined. The interpretation of the faults is also carried out with the help of a digital computer the printer of which delivers a direct report on the location and type of the faults.

The probes can be installed on trucks, rolling on the rails, and kept in sound contact with the metal of the rail by means of a film of water. It is also possible to use probes placed in a wheel rolling on the rail, the sound contact between the probe and the running surface being provided for example by a liquid enclosed in the wheel, as described in the U.S. Pat. No. 4,165,648.

The probes to be used and their positioning are determined by the characteristics of the faults to be detected. In use, it is important for each probe to remain constantly and accurately positioned with respect to the rail of the sounded track.

For probes working with a beam reflected at non-zero incidence under the rail bottom, the longitudinal spacing must be a function of the height of the rail for good reception. For probes to be used for looking for faults in the relatively narrow rail web, it is their transverse positioning with respect to the axis of the rail that must be accurately provided.

In certain existing embodiments, the lateral positioning of the probes with respect to the rail is produced by the forced pressure, by a jack or a spring, of a mechanical part rigidly connected to the probe carrying truck, against the internal lateral surface of the rail head considered as a transverse geometrical reference of the profile of the rail.

These embodiments have large disadvantages associated with the diversity in the widths of the rail heads of rails laid on the track, arising as much from the different types of rail laid as from the various degrees of lateral wear or excess width due to the crushing of the rail heads. The probes are therefore poorly positioned and cannot guarantee good testing quality.

On certain embodiments there are manual controls for the transverse and/or longitudinal positioning of the probes. These equipments are not however satisfactory, since these controls must be operated according to a visual observation of the state of the rail head, which can only lead to an approximate result and is deceptive above a certain speed of movement of the testing vehicle.

U.S. Pat. No. 4,044,594 describes a device for sounding a rail by means of a single probe housed in a wheel, necessitating a complex adjustment system to correct the lateral variations and the angular variations of the wheel resulting from irregularities in the surface of the rail. Such a device cannot operate efficiently at relatively high speeds.

SUMMARY OF THE INVENTION

The present invention uses sliding probes and its purpose is to enable the automatic positioning of the probes in their optimum positions with respect to the rail head in order to prevent the previously mentioned disadvantages of exiting devices.

The invention therefore relates to a method for the non-destructive testing of the rails of railroad tracks, in situ and continuously, as well as to a simple and efficient apparatus designed for the automatic implentation of such a method on a vehicle moving along the rail at a speed of about 40-50 km/h.

According to the method of the testing, on the track and continuous, of a rail of invention, the rail is sounded using the beam of ultrasonic waves transmitted and picked up by at least one sliding transmitting and/or receiving probe, in contact with the surface of the rail head and carried by a truck rolling on the rail. This method is distinguished by the fact that the position of at least one probe with respect to the truck is modified in order to maintain an optimum relative position of the probe with respect to the rail, and by the fact that these variations in position of the probe are controlled by the variations in the intensity of an ultrasonic beam reflected, under normal operating conditions, by the lower surface of the cushion of the sounded rail.

According to a preferred form, at least two sliding probes are used and their transverse position with respect to the truck is modified in order to keep them in the median plane of the rail, and the distance separating one from the other is modified, according to the height of the rail.

The apparatus of the invention includes a truck rolling on the rail and drawn by a railroad vehicle; this truck carries at least one sliding transmitting and/or receiving ultrasonic probe in contact with the surface of the rail head. This apparatus is distinguished by the fact that at least one probe is movable with respect to this truck, and that it includes means of actuating this probe in its movements as well as means of controlling these means of actuating depending on the variations in the energy received by the receiving probe.

BRIEF DESCRIPTION OF THE DRAWINGS

The characteristics and advantages of the invention will apppear in more detail in the following description, relating to two embodiments of the device, given by way of non-limiting example, with reference to the appended drawings.

FIG. 1 shows a side view of a probe-carrying truck carrying probes for the exploitation of a beam with a reflection at a non-zero incidence under the cushion of the rail and fitted with a device causing a displacement in the direction of the axis of the rail of a transmitting probe with respect to a receiving probe for the automatic adjustment of the distance separating these two probes depending on the actual height of the rail.

FIG. 2 shows a block diagram of an electronic control circuit for the displacement of the probes with respect to the probe-carrying truck.

FIG. 3 shows a front view of a probe-carrying truck carrying transmitting and receiving probes to be used for searching for faults in the rail web and fitted with a device causing a displacement of the probes with respect to the truck in a transverse direction with respect to the rail in order to maintain these probes in a position centered over the rail web.

DETAILED DESCRIPTION OF THE PREFERRED EMBODIMENTS

Transmitting and receiving probes are used for sounding the rail, working in pairs and using an ultrasonic beam transmitted at non-zero incidence reflecting on the lower surface of the cushion of the rail, the spacing between the probes, or their inclination, being adjusted according to the height of the rail.

The method according to the present invention consists in automatically controlling the transverse position of the probes transmitting and receiving ultrasonic waves with respect to the median plane or web of the rail and/or the position of these probes according to the height of the rail.

In order to achieve this control, at least one probe is mounted in a way that is movable in a transverse, longitudinal or angular way respectively with respect to the probe-carrying truck, and means are provided for modifying the position of the probes or of at least one of them with respect to this probe-carrying truck. In order to control the means modifying the position of the probes, ultrasonic transmitting and receiving probes are used that are placed on the running surface of the rail head and the said means of moving these probes are controlled with a signal depending on the energy received by the receiving probe.

In order to allow the sounding of the rail that is independent of the variations in height of this rail, a transmitting probe is used whose ultrasonic beam passes through the head and the web of the rail, forming with the longitudinal axis of the rail an angle of about 30° to 40°. This incident beam is reflected by the lower surface of the cushion of the rail and is returned towards the running surface of the rail. The distance separating the points of intersection of the running surface of the rail with the transmitted and reflected beams obviously depends on the height of the rail. Thus, if the distance separating the receiving probe from the transmitting probe corresponds with height of the rail, the energy received will be a maximum. It is possible to control means of moving the probes with respect to each other in the direction of the axis of the rail depending on the energy level received by the receiving probes.

It is also possible to ensure an optimum reception level, whatever the height of the rail may be, by modifying the inclination of the axis of the transmitting probe with respect to the longitudinal axis of the rail. The means modifying the inclination of the transmitting probe are also controlled by the variations in the energy received by the receiving probe.

In order to maintain the probes aligned in the median plane of the rail the transmitted ultrasonic beam is sent perpendicularly to the running surface of the rail, it propagates over the entire height of the rail and, if the probes are correctly positioned, it is reflected by the lower surface of the cushion of the rail, passes through the web and the head of the rail again and is picked up by the receiving probe. If the transverse positioning of the probes is faulty, the ultrasonic beam is reflected by the lower surface of the cushion of the rail and is deflected laterally, this surface not being perpendicular to the transmitted rays. It follows that the energy picked up on return is zero or much lower because of these parasitic reflections than if the probes are correctly positioned. The control of the means of moving the probes is thus achieved by a signal which depends on the received ultrasonic energy and this enables the probes to be permanently maintained in the longitudinal plane of the rail.

A first embodiment of the apparatus for the non-destructive testing of the rails of a railroad track including a control of the distance, considered in parallel to the axis of the rail, separating a transmitting probe from a receiving probe depending on the height of the rail is shown in FIGS. 1 and 2.

This apparatus includes a probe-carrying truck (1) connected in a known and not shown way to the bogie of a railroad track test vehicle. This truck (1) rolls on the rail (2) by means of adjustable height railwheels (3). This truck (1) includes a support (4) carrying the transmitting and receiving probe of probes respectively, in sound contact with the rail, to be used for the detection by ultrasonics of certain special faults in the rail using an ultrasonic beam with a reflection at non-zero incidence under the cushion of the rail. These sounding probes work in transmitting-receiving pairs, and the distance separating them depends on the height of the rail. The receiving and transmitting probes respectively are carried by a slide (5) sliding over one or more longitudinal guides (6) of the truck (1). These guides (6) are integral with the truck (1) and run parallel to the longitudinal axis of the rail (2).

The apparatus includes a transmitting or receiving positioning probe (7) carried by the support (4) and a receiving or transmitting probe (8), carried by the slide (5). All the rail sounding probes as well as the positioning probes (7) and (8) are arranged on the truck (1) in such a way that their active surfaces are in close and continuous contact with the upper surface of the rail (2). The positioning probes (7) and (8) can of course also serve as rail sounding probes.

The slide (5) is connected to the truck (1) by means of a jack (9) whose cylinder is hinged on the truck (1) while the piston is hinged on the slide (5). This jack is activated by means of a fluid under pressure coming from a hydraulic or pneumatic suppply set (10) delivering fluid under pressure to the jack cylinders (9) via a servo-valve (11). By means of this actuating device (9, 10, 11), it is possible to modify the distance D separating the probes (7) and (8) in parallel to the axis of the rail (2).

The servo-valve (11) is controlled by an electronic device whose functional block diagram is given in FIG. 2.

This electronic device includes a memory unit (12) fed by the signal R from the receiving probe (8), and storing the value of this signal R at time t which is proportional to the energy of the reflected ultrasonic beam r at time t. At the end of a time interval Δt, the value stored in the memory (12) is transferred into a memory (13) which stores this value Rt while memory

(12) stores the value R(t+ΔT). A comparator (14) compares the values stored in memories (12) and (13) and delivers a signal i whose amplitude corresponds with the difference ΔR={R(t+Δt)−Rt} and also a signal s indicating the sign of the difference ΔR. The signal s is stored in a memory (15) controlling a sign inverter (16), while the signal i controls a power amplifier (17) via the sign inverter (16). The amplifier (17) controls the servo-valve (11).

In normal operation, the intensity and the angle of incidence of the ultrasonic beam e transmitted by the probe (7) are constant, and if the distance D separating the probes (7) and (8) corresponds with the height H of the rail, the reflected beam r strikes the center of the probe (8) in such a way that the signal R that it delivers is a maximum.

When the truck (1) is moved along the rail (2), and as long as the height H of that remains constant, the received signal R remains constant at its maximum value and the difference ΔR is zero, such that the servo valve (11) is maintained in its rest state in which none of the jack cylinders (9) are fed with fluid.

The distance D separating the probes of a same pair and particularly probe (7) from probe (8) therefore remains unchanged.

If the height of the rail (2) is changed to H', the reflected beam r' no longer arrives or only partially arrives at the probe (8) and the signal (R) reduces in absolute value such that the difference ΔR is no longer zero and its sign (as from the second measuring interval) corresponds with an increase or a reduction in the height H of the rail (2). This signal ΔR therefore commands a displacement of the slide (5) by means of the jack (9), the servo-valve (11) and the amplifier (17) in the direction determined by the inverter (16) such that the distance D' corresponds with the height H' of the rail (2) for which the reception of the reflected beam is maximum.

In order that the probe displacement control may be independent from rail faults and therefore from high frequency variations in the intensity of the received beam, a low pass filter can be provided which eliminates these instantaneous variations.

In this way the distance D separating two probes of a same pair is servo-controlled by the actual height of the rail (2). Under these conditions the differences in reception level of the probes carried by the slide (5) are independent from the variations in the height of the rail and correspond with faults in the rail (2).

Instead of modifying the distance D between a transmitting probe and the receiving probe associated with it, it is possible to modify the inclination, or angle of incidence, of the transmitted beam according to the height H of the rail.

A second embodiment of the apparatus for the non-destructive testing of the rails of a track incorporating a control of the transverse position of the probes with respect to the probe-carrying truck is shown in FIG. 3.

This apparatus includes a probe-carrying truck (1) connected in a known and not shown way to the bogie of a railroad track test vehicle, rolling on the rails (2) of the track by means of railwheels (3). Above each line of rail (2), the truck (1) incorporates one or more guides (18) running parallel to the plane of the track and perpendicular to the axes of the lines of rail (2) and which serve as a support for a slide (19) sliding over this guide or these guides (18), carrying the ultrasonic transmitting and receiving probes in sound contact with the rail, used for sounding the rails (2) and whose transverse position with respect to the rail is determinant for good sounding of the faults that they have to detect.

This slide (19) again carries a transmitting-receiving ultrasonic probe (20) maintained in contact with the upper surface of the rail (2). This probe (20) transmits a beam of ultrasonic waves (e') (FIG. 2) perpendicular to the running surface of the rail (2) which, when the probe (20) is in the median plane of the rail, passes through the head and the web of the rail, is reflected back on itself in r' at the lower surface of the cushion of the rail and passes through the web and the head of the rail before being picked up. The received energy is at a maximum under these conditions. If however, the probe is transversely shifted out of the median plane of the rail, parasitic reflections at the lower lateral surfaces of the rail head reduce the intensity of the reflected beam picked up by the probe (20).

The described apparatus also includes means of transverse displacement of the slide (19) comprising in the example shown a jack (21) whose cylinder is hinged on the truck (1) and the piston on the slide (19), fed with fluid under pressure from a supply set (10) by means of servo-valves (22).

These servo-valves (22), depending on their states, enable either the locking of the jack (21) in its position, or the feeding of one or other of its cylinders thus causing a displacement in one direction or the other of the slide (19). These servo valves (22) are controlled by an electronic device, driven by the received reflection beam signal r' delivered by the transmitting-receiving probes (20), whose functional block diagram is identical with that of FIG. 2 except that the probes (7) and (8) are replaced by the transmitting-receiving probe (20), normal to the surface of the rail, and that the amplifier (17) controls the servo-valve (22) and therefore the jack (21) controlling the transverse displacements of the transverse slide (19).

In this way the probes carried by the transverse slide (19) are maintained in the median plane of the rail (2).

It is obvious that in an embodiment that is not shown, the apparatus can combine the described transverse and longitudinal controls, the guides (6) being carried by the slide (19) and not by the truck directly for example.

In another variant, the jacks (9,21) can be replaced with stepper motors modifying the positions of the slides (5, 19) respectively.

It is also possible to use the ultrasonic transmitting-receiving probes controlling the means of displacement simultaneously as rail fault sounding probes.

In the case in which the energy transmitted by the transmitting probe is not constant, the ratio between the transmitted energy and the received energy is used to control the displacement of the probes.

I claim:

1. A method for non-destructively and continuously testing railroad track rails, in situ, to determine the presence of faults, comprising the steps of:
    (a) transmitting a beam of ultrasonic waves into a rail using a first transducer disposed in sliding contact with an upper surface of the rail,
    (b) receiving signals of said beam reflected by a lower surface of the rail using a second transducer disposed in sliding contact with the surface of the rail,
    (c) comparing time displaced reflected signals to determine the magnitude and direction of any changes in the strength of the reflected signals, and (d) displacing said second transducer in a direction parallel to the longitudinal direction of the rail in accordance with the comparison determinations to maximize the strength of the reflected signals and to thereby compensate for any variations in the height of the rail.

2. A method for non-destructively and continuously testing railroad track rails, in situ, to determine the presence of faults, comprising the steps of:
   (a) transmitting a beam of ultrasonic waves into a rail using a first transducer disposed in sliding contact with an upper surface of the rail,
   (b) receiving signal of said beam reflected by a lower surface of the rail using a second transducer disposed in sliding contact with the upper surface of the rail,
   (c) comparing time displaced reflected signals to determine the magnitude and direction of any changes in the strength of the reflected signals, and
   (d) modifying the inclination of the beam of ultrasonic waves transmitted by said first transducer in the median longitudinal plane of the rail in accordance with the comparison determinations to maximize the strength of the reflected signals and to thereby compensate for any variations in the height of the rail.

3. A method for non-destructively and continuously testing railroad track rails, in situ, to determine the presence of faults, comprising the steps of:
   (a) transmitting a beam of ultrasonic waves into a rail using a first transducer disposed in sliding contact with an upper surface of the rail,
   (b) receiving signals of said beam reflected by a lower surface of the rail using a second transducer disposed in sliding contact with the upper surface of the rail,
   (c) comparing time displaced reflected signals to determine the magnitude and direction of any changes in the strength of the reflected signals, and
   (d) displacing said first or said second transducer in a direction perpendicular to the median longitudinal plane of the rail in accordance with the comparison determinations to maximize the strength of the reflected signals and to thereby compensate for any variations in the lateral disposition of a transducer thereon.

4. An apparatus for non-destructively and continuously testing railroad track rails, in situ, to determine the presence of faults, comprising: a truck (1) disposed in rolling contact with a rail (2), a first transducer (7) mounted on said truck in sliding contact with an upper surface of the rail for transmitting a beam (e) of ultrasonic waves into the rail, a second transducer (8) mounted on said truck in sliding contact with the upper surface of the rail for receiving signals (r, r') of said beam transmitted by said first transducer after their reflection from a lower surface of the rail, and means (9-11) for displacing said second transducer in a direction parallel to the longtudinal direction of the rail to maximize the strength of the received signals.

5. An apparatus according to claim 4, wherein said means for displacing said second transducer (8) comprise a slide (5) which is able to slide on a guide (6) parallel to the longitudinal direction of the rail (2) and on which said second transducer is mounted, a jack (9) acting on said slide to displace it along said guide, an actuating device (10,11) for controlling the displacements of a piston from said jack, and electronic means (12-17) for controlling said actuating device so as to maximize the strength of the signals received by said second transducer.

6. An apparatus for non-destructively and continuously testing railroad track rails, in situ, to determine the presence of faults, comprising: a truck (1) disposed in rolling contact with a rail (2), a first transducer (7) mounted on said truck in sliding contact with an upper surface of the rail for transmitting a beam (e) of ultrasonic waves into the rail, a second transducer (8) mounted on said truck in sliding contact with the upper surface of the rail for receiving signals (r, r') of said beam transmitted by said first transducer after their reflection from a lower surface of the rail, and means for modifying the inclination of the beam (e) of ultrasonic waves transmitted by said first transducer in the median longitudinal plane of the rail to maximize the strength of the received signals.

7. An apparatus for non-destructively and continuously testing railroad track rails, in situ, to determine the presence of faults, comprising: a truck (1) disposed in rolling contact with a rail (2), a transmitting-receiving ultrasonic transducer (20) mounted on said truck on sliding contact with an upper surface of the rail, and means (19,21) for displacing said transducer in a direction perpendicular to the median longitudinal plane of the rail to maximize the strength of signals received by the transducer.

8. An apparatus according to claim 7, wherein said means for displacing said transducer (20) comprise a slide (19) which is able to slide on a guide (18) perpendicular to the median longitudinal plane of the rail and on which said transducer is mounted, a jack (21) acting on said slide to displace it along said guide, an actuating device (10,22) for controlling displacements of a piston of said jack, and electronic means (12-17) for controlling said actuating device so as to maximize the strength of the signals received by said transducer.

* * * * *